United States Patent [19]

Robert et al.

[11] Patent Number: 4,786,744

[45] Date of Patent: Nov. 22, 1988

[54] METHOD FOR OPENING THE GEM DICYANO EPOXIDES AND THE FORMATION OF COMPOUNDS THEREFROM

[75] Inventors: Albert L. F. Robert, Rennes; Jean-Luc Guinamant, Neuilly; Sylvie C. A. Jaguelin, Neuilly sur Seine, all of France

[73] Assignee: Centre National De La Recherche Scientifique, Paris, France

[21] Appl. No.: 745,579

[22] Filed: Jun. 17, 1985

[30] Foreign Application Priority Data

Jun. 15, 1984 [FR] France .................................. 8409434

[51] Int. Cl.[4] .................... C07C 102/08; C07C 67/22; C07C 51/08

[52] U.S. Cl. .......................................... 558/14; 560/23; 560/60; 560/105; 562/496; 564/124; 564/166; 564/182; 564/209; 260/545 R

[58] Field of Search ............... 564/124, 166, 182, 209; 260/545 R; 562/496; 560/105, 60, 23; 558/14

Primary Examiner—Richard L. Raymond
Assistant Examiner—Carolyn Greason
Attorney, Agent, or Firm—Scully, Scott, Murphy and Presser

[57] ABSTRACT

The invention relates to a method for opening the ring of gem dicyanepoxides comprising reacting a gem dicyanepoxide with a mononucleophilic compound in the presence of a hydrohalic acid or a weakly nucleophilic acid.

8 Claims, No Drawings

METHOD FOR OPENING THE GEM DICYANO EPOXIDES AND THE FORMATION OF COMPOUNDS THEREFROM

The present invention relates to a novel method for opening the ring of the gem dicyanoepoxides. The invention also relates, in one of its forms of implementation, to the preparation of arylacetic, arylpropionic and heterocyclic compounds from gem dicyanoepoxides. And finally the invention has as its object certain new compounds obtained through the implementation of these methods.

We know that the reaction of epoxides with hydrochloric acids causes the epoxide ring to open and leads to generally stable chlorohydrins.

The opening of the epoxide rings of the gem dicyanoepoxides by thiocarbonyl derivatives has also been the object of various studies (See "Obtaining Tetrahedral Intermediates During the Reaction of Gem Dicyanoepoxides with Substituted Thioamides. Evolution of these Intermediaries into Mesoionic Thiazoles", M. Baudy and A. Robert, *Tetrahedron Letters*, Vol. 21, pp. 2517–2520, 1980; see also "A General Synthesis of Ring-Fused Mesoionic Thiazolines from 2,2-Dicyanooxiranes under Neutral Conditions", M. Baudy-Floc'h, A. Robert, *Synthesis*, No. 12, December 1981, pp. 981–984).

As they continued their study of the opening of the rings of gem dicyanoepoxides, the inventors of the present invention confirmed that these compounds are able to react with mono- or binucleophilic compounds in the presence of a hydrohalic acid, to lead to various families of compounds, e.g., arylacetic or arylpropionic compounds in particular, when the reagent is mononucleophilic, and to heterocyclic compounds, in particular, the family of thiazoles and imidazoles when the reagent is bi-nucleophilic.

One aim of the invention, therefore, is to propose a method for opening the gem dicyanoepoxide ring.

Another aim of the invention is to propose new methods of synthesis of derivatives of arylacetic and arylpropionic acids and of heterocyclic compounds, in particular, derivatives of the thiazole and imidazole families.

And finally, another aim of the invention is to obtain new compounds in the families mentioned above.

With this in mind, the object of the invention is a method for opening the gem dicyanoepoxide ring, comprising the reaction of the gem dicyanoepoxide with a mononucleophlic compound in the presence of an acid chosen from the group comprising the hydrohalic acids and the weakly nucleophilic acids.

The method according to the invention therefore consists in reacting, selectively, in one stage, two different nucleophilic reagents—the hydrohalic acids and a second nucleophile—on epoxides substituted with two cyano groups. As a matter of fact, unlike the classic opening of epoxides by hydrohalic acids, which leads to stable chlorohydrins, we have confirmed, although the validity and scope of the present invention are not linked to this theory, that the gem dicyanoepoxides react with hydrohalic acids to form unstable cyanohydrins that evolve instantaneously into intermediates that are of particular interest, because they are substituted by a cyanoformyl group, which makes the intermediates very reactive compounds. The second nucleophile present in the medium reacts immediately with this intermediate to lead, with very good yields, to a large number of these compounds, some of which are new.

Using H X to designate the hydrohalic acid and Nu H for the second nucleophilic reagent, the result will be the formula below when Nu H is a mononucleophilic reagent:

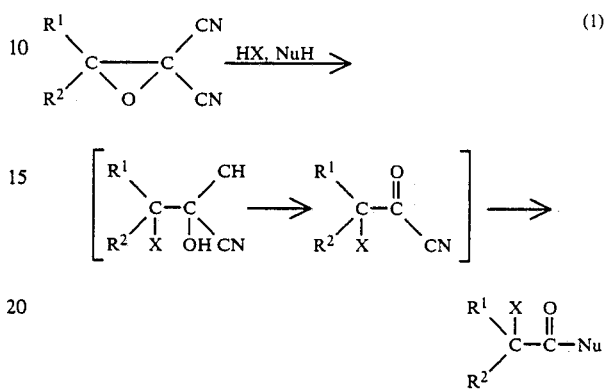

In this reaction the two nucleophiles are X and Nu, and X can be a halide ion (Cl, Br, F) and Nu is some other nucleophile such as an alcohol or an amine. Due to the disubstitution by cyano groups on the epoxide ring, the cleavage of the epoxide is specifically oriented. X always and exclusively substitutes on the carbon bearing the groups $R^1$ and $R^2$. Moreover, the second nucleophile present in the medium (alcohol or amine) does not participate in the opening of the epoxide cycle, but always reacts with the intermediate bearing the cyanoformyl group.

This double selectivity is at the origin of the quasi-quantitative yields in halogen derivatives.

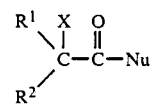

In the case where Nu H is a mononucleophilic reagent, reaction (1) above is therefore reduced to the selective addition of two nucleophiles (X and Nu) on the two carbons of the ring, while the two cyanide ions are eliminated.

The conditions of implementation of the method according to the invention, (temperature, pressure, pH, relative quantities of reagents) are not critical in nature.

Among the numerous compounds that can be prepared by reaction (1), the inventors made a particular study of the derivatives of arylacetic and arylpropionic acids.

Therefore, another object of the invention is a method for preparing arylacetic and arylpropionic acids and their derivatives by reacting a gem dicyanoepoxide, wherein the other ring carbon atom bears an aryl group, with a nucleophilic reagent, such as water, alcohols, and amines. The products of this reaction are alpha-halogenated esters, the alpha-halogenated arylacetic or arylpropionic acids and the corresponding alpha-halogenated arylacetic or arylpropionic amides.

This reaction is written:

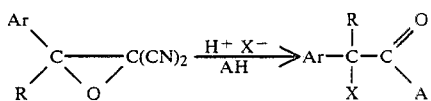

with X=Cl, Br or F and A=OH, OR, NHR. or X=A-=OR.

When the hydrohalic acid is hydriodic acid in aqueous solution or hydroalcoholic solution its reaction with the gem dicyanoepoxide (with R=H) leads directly to non-halogenated arylacetic acid or the ester thereof, respectively. The intermediate halogen derivative is directly reduced by HI present in the medium, as shown by the reaction diagram below:

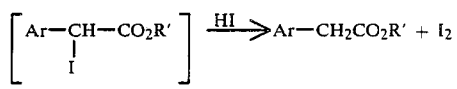

Another object of the invention therefore is a method of preparation of an arylacetic acid, which comprises the reaction of a gem dicyanoepoxide wherein one carbon bears an aryl group and a hydrogen atom, with an alcohol in the presence of hydriodic acid.

Although the alcohols are not acidic enough to open the rings of the epoxides, the hydrohalic acid HX and the second mononucleophile Nu H of reaction (1) above can be one and the same compound (X=Nu=OR), provided the reaction takes place in the presence of a weak nucleophilic acid such as paratoluenesulfonic acid.

Another object of the invention, therefore, is a method for preparing alpha-alkoxy arylacetic esters, comprising the reaction of a gem dicyanoepoxide, in which one carbon atom bears an aryl group and a hydrogen atom, with an alcohol in the presence of a weakly nucleophilic acid, such as paratoluenesulfonic acid.

This reaction is written:

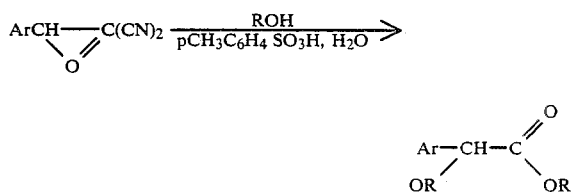

A detailed description of various forms of implementation of the invention and examples of application of the methods mentioned above will be presented below. It is understood that this description is intended only to illustrate the invention and is nonlimiting in nature.

Reference is made, first of all, to the synthesis of arylacetic or arylpropionic acids and their derivatives through the application of the methods of the present invention.

As indicated above, the reaction diagram of the method in this application is the following:

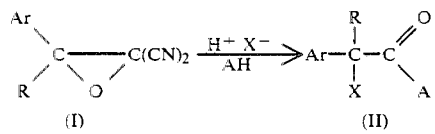

in which Ar designates an aryl group and R another group with X=Cl, Br or F and A=CH, OR, NHR, or X=A=OR.

The initial gem dicyanoepoxides can easily be obtained by the following successive reactions, which are well known in the art:

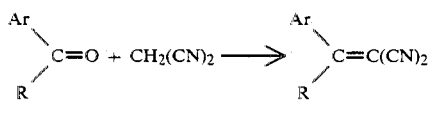

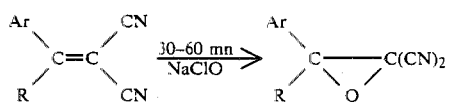

1. Synthesis of alpha-halogenated esters (II)

The alpha-halogenated esters II (with X=Cl or Br) were obtained with good yields by simple reaction of epoxides I with an alcohol, in the presence of an aqueous solution of a hydrohalic acid in stoichiometric quantities. The reaction was complete after 3 hours of reflux. The alpha-fluorinated esters II (X=F) were prepared by reaction of hydrofluoric acid in solution in pyridine, with epoxides of Formula I. The latter were obtained quasi-quantitatively by reaction of Javel water with the corresponding ethylene compounds which in turn result from the condensation of an aldehyde or a ketone with malononitrile (quasi-quantitative yield).

The hydrohalic acid can be HCl or HBr in aqueous solution or HF in solution in pyridine. It is used in slight excess relative to the stoichiometric amounts.

EXAMPLE I

The synthesis of the ester II with Ar=pClC6H4; R=(CH3)2CH; X=Br is described by way of example.

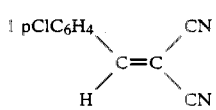

35 g (0.25 mol) of p-chlorobenzaldehyde and 16.5 g (0 25 mol) of malononitrile were placed in solution in 120 cc of dioxane. Piperidine (2 cc) was added and the mixture was stirred at ambient temperature for 30 minutes. The ethylene compound precipitated on the addition of 300 cc of water. The precipitate was filtered, washed in water, then dried (M.P.=160° C., yield 96%). This compound was pure enough to be used directly in the subsequent stage.

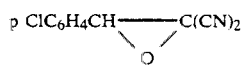

20 g (0.10 mol) of the ethylene 1 compound were put in solution in 100 cc of acetonitrile. The pH of the solution was adjusted (with pH paper) to 5-6 by addition of 2N sulfuric acid. 200 cc of 2.5N sodium hypochlorite in fractions of 5 cc was added and with vigorous stirring at ambient temperature and the pH was maintained at close to 5-6 by the addition of 2N H$_2$SO$_4$ (a total of 20 cc of 2N H$_2$SO$_4$). The agitation was maintained for 30 min; then the solution was diluted with one liter of water. The epoxide that precipitated was filtered, collected, and washed with water several times before being dried (M.P.=128°-129° C., yield 96%). The epoxide thus obtained was used with no other purification in the following reaction.

Synthesis of the ester II

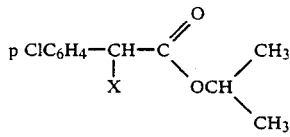
1c 1 g of epoxide (5×10$^{-2}$ mol) was put in solution in 30 cc of isopropanol. 1 cc of 48% hydrobromic acid was added and the reaction was refluxed for 3 hours. After evaporation of the isopropanol, the crude product was dissolved in ether. The product was extracted with water and the ether layer containing the product was dried on sodium sulfate. The oil obtained after evaporation of the ether corresponded to practically pure ester II (yield 85%). The ester II was dried with the aid of a Buchi tubular furnace (furnace temperature 110° C., P=1.5×10$^{-2}$ mbar).

Table I below shows the characteristics of other chlorine- or bromine-rich esters II, prepared according to the same method of operation. In this table as in the tables which will follow, the compounds prepared are characterized by their infrared IR, nuclear magnetic resonance(NMR), and mass spectra. In the various tables, the compounds designated by the sign * are new, as far as the inventors know, and as such constitute an object of the invention.

Synthesis of ester II of the formula

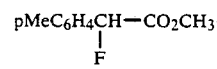

The fluorine-rich ester for which Ar=pCH$_3$C$_6$H$_4$, R=H and R'=CH$_3$ was prepared according to the following method of operation:

1 g of epoxide I (Ar=pMeC$_6$H$_4$, R=H) was put in solution in 10 cc of dichloromethane. 20 cc of a solution of HF (70 g)/pyridine (30 g) was then added and the solution was refrigerated (2° C.) for 3 days. After addition of 50 cc of methanol, the reaction medium was neutralized by a 28% solution of ammonia. The product was extracted in ether and dried. After the ether was evaporated off, an alpha-fluorinated ester was obtained: BP=70° C. @1×10$^{-2}$ mbar, yield 80%.

TABLE I

α-halogen Esters  I(R = H) ArCH—C(=O)(OR') with X  (1)

| Ar | R' | X | % Yield (1) | B.P. P mbar | Formula | MW (g)/ th tr | IR(Film liq.) νCO(cm$^{-1}$) | NMR CuCl$_3$/TMS R' | δ (ppm) Ar |
|---|---|---|---|---|---|---|---|---|---|
| mNO$_2$C$_6$H$_4$ | (CH$_3$)$_2$CH | Br | 85 | 135 2 10$^{-2}$ | C$_{11}$H$_{12}$NO$_4$Br | 300.9949 300.994 | 1730 | 1.30(d,3H) 1.37(d,3H) 5.10(m,1H) 5.40(s,1H) | 7.45–8 50(m,4H) |
| pCH$_3$C$_6$H$_4$ | C$_2$H$_5$ | Br | 86 | 105 3 10$^{-2}$ | C$_{11}$H$_{13}$BrO$_2$ | 256.0098 256.008 | 1743 | 1.22(t,3H) 2.30(s,3H) 4.17(q,2H) 5.30(s,1H) | 7.05–7 47(m,4H) |
| pCH$_3$C$_6$H$_4$ | CH$_3$ | F | 80 | 70 2 10$^{-2}$ | C$_{10}$H$_{11}$FO$_2$ | — | 1757 | 2.35(s,3H) 3.72(s,3H) 5.72(d,1H JHF = 47 Hz) | 7.00–7 50(m,4H) |

Similarly, Table II below shows the characteristics of various propionic alpha-halogen esters and propionic esters which are derived therefrom by reduction with zinc in acetic acid-water medium.

TABLE II

Propionic Esters

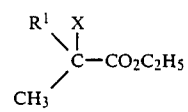

| R$^1$ | X | % Yield | NMR (CDCl$_3$) δ$_{ppm}$ | IR film liq. cm$^{-1}$ |
|---|---|---|---|---|
| C$_6$H$_5$ | Cl | 90 | 1.20 (t, 3H), 2.12 (s, 3H) 4.30 (q, 2H) 7.10–7.70 (m, 5H) | 1726 |
| mBrC$_6$H$_4$ | Cl | 70 | 1.27 (t, 3H), 2.12 (s, 3H) 4.25 (q, 2H) 7.00–7.90 (m, 4H) | 1730 |
| C$_6$H$_5$—CH$_2$ | Br | 80 | 1.30 (t, 3H), 1.85 (s,3H) 3.50(centre syst AB, 2H)4.25(q, 2H) 7.25 (s, 5H) | 1728 |
| CO$_2$C$_2$H$_5$ | Cl | 80 | 1.32 (t, 6H), 1.94 (s,3H) 4.30(q, 4H) | 1741 |
| C$_6$H$_5$ | H | 90 | 1.22 (t, 3H), 1.52 (d, 3H) 3.72 (q, 1H) 4.12 (q, 2H) 7.10–7.60(m,5H) | 1728 |
| mBrC$_6$H$_4$ | H | 70 | 1.23 (t, 3H) 1.52 (d, 3H) 3.70 | 1728 |

TABLE II-continued

Propionic Esters $$\begin{array}{c} R^1 \quad X \\ \diagdown \mid \\ C-CO_2C_2H_5 \\ \diagup \\ CH_3 \end{array}$$

| $R^1$ | X | % Yield | NMR (CDCl$_3$) $\delta_{ppm}$ | IR film liq. cm$^{-1}$ |
|---|---|---|---|---|
| CO$_2$C$_2$H$_5$ | H | 80 | (q,1H) 4.15 (q, 2H) 7.00-7.60(m,4H) 1.30 (, 6H), 1.45 (d, 3H) 3.45 (q, 1H) 4.42 (q, 4H) | 1730 |

By way of example of the preparation of propionic esters, the synthesis of the ethyl 2-chloro-2-phenyl propionate of the formula will now be described.

EXAMPLE 2

1 g of alpha-halogenated ester $$\begin{array}{c} Cl \\ \mid \\ (Ph-C-CO_2Et) \\ \mid \\ CH_3 \end{array}$$

was put in solution in 20 cc of acetic acid and 10 cc of water. 3 g of powdered zinc was added and the reaction was refluxed for 4 hours. 250 cc of water was added, and the product was extracted with ether (4×50 ml). The ether phase was washed with dilute sodium bicarbonate, then with water. The ether was dried on sodium sulfate and then evaporated. The oil obtained was pure, as determined by NMR. The reaction yield was quantitative and the compound was characterized by its IR and NMR spectra (Table II).

Table II shows that the method according to the invention produces ethyl alpha-chloro-alpha-methyl malonate (R=CO$_2$Et, X=Cl) or its reduced derivative (R=CO$_2$Et, X=H) and hence constitutes a means of synthesizing monoalkyl derivatives of ethyl malonate (such compounds cannot be prepared selectively by direct alkylation of ethyl malonate). The inventors also prepared ethyl phenyl malonate under similar conditions and in a similar fashion.

(2Synthesis of arylacetic esters Ar—CH$_2$CO$_2$R'

Synthesis of the ester Ph—CH$_2$CO$_2$C$_2$H$_5$ is given by way of example.

$$\begin{array}{c} Ph \diagdown \quad O \quad \diagup CN \\ C———C \\ \diagup \quad \diagdown \\ CO_2Et \quad CN \end{array} \xrightarrow[(2°) \text{ Zn/CH}_3\text{CO}_2\text{H}]{(1°) \text{ HCl,EtOH}} \begin{array}{c} \diagup CO_2Et \\ Ph-CH \\ \diagdown CO_2Et \end{array}$$

EXAMPLE 3

1 g of epoxide I (Ar=Ph) prepared according to the method of operation described above (1a) (with replacement of p-chlorobenzoic aldehyde by benzoic aldehyde) was placed in solution in 30 cc of ethanol. 1 cc of 67% hydriodic acid was added and the solution was refluxed for two hours. After evaporation of the ethanol the residual oil was dissolved in ether, and the ether was washed with a solution of thiosulfate until the purple color disappeared. The ether was dried over anhydrous soldium sulfate and then evaporated. An NMR spectrum of the oil showed that the product was relatively pure. The ester thus obtained (yield 70%, not optimized) showed the same IR and NMR spectra as a sample of commercial ethyl phenylacetate.

3 Synthesis of alpha-halogenated arylacetic acids

The alpha-halogenated arylacetic acids III were obtained in a manner similar to that of the corresponding esters II (R=H), with replacement of the alcohol by tetrahydrofuran (THF).

$$\begin{array}{c} ArCH———C(CN)_2 \\ \diagdown \diagup \\ O \end{array} \xrightarrow[\text{THF}]{\text{HX, H}_2\text{O}} \begin{array}{c} ArCH-CO_2H \\ \mid \\ X \end{array} \quad \text{III}$$

The synthesis of the acid $$\begin{array}{c} Ph-CH-CO_2H \\ \mid \\ Br \end{array}$$

is described below by way of example.

EXAMPLE 4

1 g of epoxide I (Ar=Ph) in solution was mixed with THF (30 cc) and 48% HBr (1 cc) and refluxed for 3 hours. The THF was then evaporated at reduced pressure and the medium was extracted with ether. The acid was extracted from the ether phase by washing with a solution of dilute NaOH (20 cc). The aqueous phase was then acidified with HCl and the acid was extracted with ether. The ether was dried on sodium sulfate, then evaporated, and the acid obtained (m.p.=82° C.; yield 70%) was identified by comparing its characteristics (IR and NMR) with those of a commercial sample.

4 Synthesis of the alpha-halogenated arylacetic amides

The alpha-halogenated arylacetic amides IV were obtained from the reaction of the epoxides I in solution in acetonitrile in the presence of a stoichiometric quantities of a hydrohalic acid in aqueous solution and an amine. The reaction was completed after 1 hour at ambient temperature.

$$\begin{array}{c} ArCH———C(CN)_2 \\ \diagdown \diagup \\ O \end{array} \xrightarrow[\text{CH}_3\text{CN}]{\text{NH}_2, \text{ HX}} \begin{array}{c} O \\ \parallel \\ ArCH-C \quad R^1 \\ \mid \quad \diagup \\ X \quad N \\ \quad \diagdown \\ IV \quad H \end{array}$$

Table III below shows the physical data of various alpha-halogenatd arylacetic amides obtained by the method of the invention. Example 5 which follows illustrates the preparation of some of these amides.

TABLE III

α-halogenated Amides   $pX'C_6H_4-\underset{X}{CH}-C\underset{NHR^1}{\overset{O}{\nwarrow}}$

| X' | X | R¹ | % Yield | M.P. °C. | Formula | MW (g) M.+ Calc Tr | NMR δppm (CDCl₃ + CF₃CO₂H) | IR cm⁻¹ (Nujol) |
|---|---|---|---|---|---|---|---|---|
| Cl | Br | CH₃CH₂ | 90 | 120 | C₁₀H₁₁NOBrCl | 274.9712 274.91 | 1.20: (t, 3H) 3.30: (m, 2H) 5.40: (s, 1H) 7.35: (m, 4H) | νNH: 3270 νCO: 1646 |
| Cl | Br | CH₃ | 90 | 114 | C₉H₉NOBrCl | 260.9556 260.952 | 2.90: (d, 3H) 5.40: (s, 1H) 7.35: (m, 4H) | νNH: 3277 νCO: 1669 |
| H | Cl | CH₃ | 80 | 76 | C₉H₁₀NOCl | 183.0450 183.044 | 2.80: (t, 3H) 5.40: (s, 1H) 7.35: (m, 5H) | νNH: 3268 νCO: 1655 |
| Cl | Cl | C₆H₅ | 96 | 122 | C₁₄H₁₁NOCl₂ | 279.0217 279.021 | 5.57: (s, 1H) 7.35: (m, 9H) | νNH: 3265 νCO: 1669 |
| Cl | Cl | CH₃CH₂ | 76 | 106 | C₁₀H₁₁N³⁵Cl³⁷Cl | 233.0188 233.021 | 1.20: (t, 3H) 3.35: (m, 2H) 5.35: (s, 1H) 7.35: (s, 4H) | νNH: 3277 νCO: 1665 |
| Me | F | H | 40 (non optimise) | 133 | C₉H₁₀FNO | 167 0746 167 074 | 2.40 (d, 3H; J$_{HF}$=2Hz) 5.77 (d, 1H; J$_{HF}$=47Hz) 7.15 a 7,35 (m, 4H) | νNH: 3380 νCO: 1656 |
| CH₃ | Cl | CH₂CH₂OH | 90 | 102 | C₁₁H₁₄NO₂Cl* | 227.0713 227.072 | 2.40 (s, 3H) 3.45 (t, 2H) 3.65 (t, 2H) 5.35 (s, 1H) 7.20 (m, 4H) | νNH: 3305 νCO: 1640 |
| Cl | Cl | CH₂CH₂Cl | 98 | 82 | C₁₀H₁₀NOCl₃* | 264.9827 264.982 | 3.70 (d, 4H) 5.40 (s, 1H) 7.35 (s, 4H) | νNH: 3270 νCO: 1646 |
| NO₂ | Cl | CH₂CH₂Cl | 92 | 90 | C₁₀H₉N₂O₃* | (M—Cl—HCl)+ 205. 0613 205.060 | 3.70 (d, 4H) 5.50 (s, 1H) 7.90 (m, 4H) | νNH: 3296 νCO: 1654 |
| H | Cl | CH₂CH₂Cl | 96 | 84 | C₁₀H₁₁NOCl₂* | 231.0217 231.021 | 3.60 (d, 4H) 5.40 (s, 1H) 7.40 (s, 5H) | νNH: 3311 νCO: 1649 |
| Cl | Cl | CH₂CH₂SCN | 70 | 106 | C₁₁H₁₀N₂OSCl₂* | 287.9891 287.988 | 3.65 (d, 4H) 5.25 (s, 1H) 7.40 (s, 4H) | νNH: 3275 νC≡N: 2149 νCO: 1635 |

*New Compound

EXAMPLE 5

4a Preparation of alpha-halogenated arylacetic amides IV with X=Cl or X=Br.

The synthesis of the amide

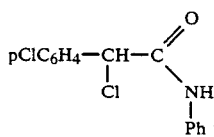

is described below by way of example.

1 g of epoxide was placed in solution in 20 cc of HCl in water. The solution was stirred at ambient temperature for 16 hours, then the water was distilled off. The residual oil was dissolved in ether and then washed in dilute sodium bicarbonate. Evaporation of the ether led to the amide M.P.=122° C., yield 96%). 4b Synthesis of alpha-fluoramide IV with X'=Me, X=F, R¹=H 1 g of epoxide I (Ar=pMeC₆H₄, R=H) was placed in 10 cc of dichloromethane. 20 cc of a solution of HF (70 g)/pyridine (30 g) was added and the reaction mixture was refrigerated (2° C.) for 3 days. The reaction medium was neutralized with 28% ammonia. The product was extracted with dichloromethane. The product was dried and the solvent was evaporated off, leaving the alpha-fluoroamide as a solid: M.P.=133° C. (ether-petroleum ether), yield 40% (not optimized).

4c Synthesis of the alpha-chlorinated amide IV with X=Cl, R¹=CH₂CH₂SCN

This compound was prepared according to the following diagram:

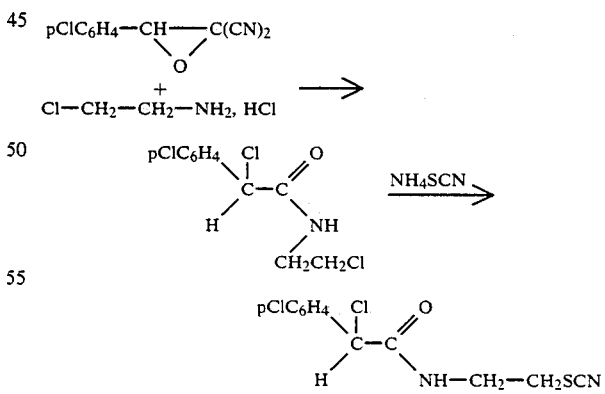

To 2 g of halogenated amide IV (X=Cl, R'=CH₂CH₂CL) (prepared according to the method of operation 4a described above) in solution in 30 cc of toluene, was added 1.5 g of ammonium thiocyanate in 20 cc of water. 0.4 g of benzyltriethylammonium chloride was added and the reaction was refluxed with stirring for 24 hours. The organic phase was separated, washed in water and dried on sodium sulfate, then evaporated. The solid, that was formed, is amide IV (R'=CH$_2$CH$_2$SCN) M.P.=106° C., yield 70%.

The amide thus obtained seems particularly interesting because the inventors have shown that this compound can be cyclized in the presence of triethylamine to form oxo-5 tetramisol.

The synthesis of the ester V with Ar=p Cl C$_6$H$_4$ and R=ethyl will be described in Example 6 below.

5 Synthesis of alpha-alkylated arylacetic esters

As indicated above, the alpha-alcoxy arylacetic esters V can be prepared according to the following process:

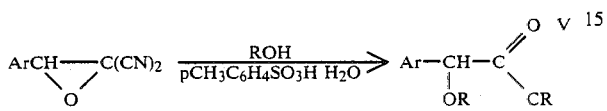

EXAMPLE 6

2 g of epoxide I (Ar=pClC$_6$H$_4$) and 3.6 g of paratoluenesulfonic acid monohydrate were refluxed for 48 hours in 30 cc of ethanol. After evaporation of the solvent, the residual oil was dissolved in 50 cc of ether and washed with 20 cc of 2N sodium bicarbonate and with water (4 times 50 ml). After drying on Na$_2$SO$_4$, the ether was evaporated. The ester,

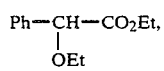

was obtained with a 65% yield, and no impurity was detected within the limits of sensitivity of the NMR.

Table V below shows the characteristics of other alpha-alkylated arylacetic esters prepared according to the invention.

group and a hydrogen atom in the presence of hydroiodic acid.

2. The process according to claim 1 wherein ethyl phenylacetate is formed.

3. A process for preparing alpha-alkoxy arylactic esters comprising reacting an alcohol with a gem dicyanoepoxide in which a ring carbon atom bears an aryl group and a hydrogen atom in the presence of a weakly nucleophilic acid.

4. The process according to claim 3 wherein the weakly nucleophilic acid is paratoluenesulfonic acid.

5. The process for the preparation of the ester of arylacetic acid of the formula

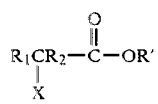

which comprises reacting a gem dicyanoepoxide of the formula

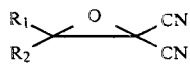

with a lower alkanol in the presence of hydrobromic acid, hydrochloric aid or hydrofluoric acid, wherein
R$_1$ is aryl;
R$_2$ is H or CH$_3$;
X is Br, Cl or F; and
R' is lower alkyl.

6. A process for preparing

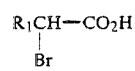

TABLE V

α-alkoxy arylacetic acid Esters

Ar—CH(OR)—CO$_2$R

| Reference | Ar | R | % Yield | Formula | FW (g) th tr | IR (film liq.) $\nu_{CO}$cm$^{-1}$ | NMR CDCl$_3$/TMS | δ |
|---|---|---|---|---|---|---|---|---|
| 29 | C$_6$H$_5$ | C$_2$H$_5$ | 60 | C$_{12}$H$_{16}$O$_3$ | 208.1099 208.110 | 1746 | 1.18 (t, 3H) 1.26 (t, 3H) 3.25 a 3,80 (m, 2H) 4.15 (q, 2H) 4.86 (s, 1H) | 7.20 a 60 (m, 5H) |
| 25 | C$_6$H$_5$ | (CH$_3$)$_2$CH— | 50 | C$_{14}$H$_{20}$O$_3$ | Observe M—CO$_2$CH(CH$_3$)$_2$ 149.0966 149.096 | 1750 1728 | 1.12 (d, 3H) 1.21 (d, 3H) 1.24 (d, 3H) 1.27 (d, 3H) 3.71 (septet, 1H) 4.94 (s, 1H) 5.04 (septet, 1H) | 7.15 a 770 (m, 5H) |
| 25 | pNO$_2$C$_6$H$_4$ | C$_2$H$_5$ | 75 | C$_{12}$H$_{15}$NO$_5$ | 253.0950 253.095 | 1745 1734 | 1.27 (t, 3H), 1.35 (t, 3H) 3.67 (m, 2H) 4.22 (q, 2H) 5.00 (s, 1H) | 7.60 a 40 (m, 4H) |
| 30 | pClC$_6$H$_4$ | C$_2$H$_5$ | 65 | C$_{12}$H$_{15}$ClO$_3$ | 242.0709 242.071 | 1743 | 1.25 (t, 3H) 1.30 (t, 3H) 3.60 (m, 2H) 4.20 (q, 2H) 4.85 (s, 1H) | 7.35 (m, 4H) |

What is claimed is:

1. A process for preparing an ester of arylacetic acid comprising reacting an alcohol with a gem dicyanoepoxide, wherein one ring carbon atom bears an aryl which comprises reacting a gem dicyanoepoxide of the formula

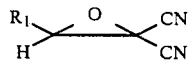

with water in the presence of hydrobromic acid wherein $R_1$ is aryl.

7. The process for preparing α-halogenated amides of the formula

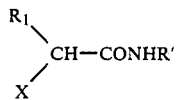

which comprises reacting a gem dicyanoepoxide of the formula

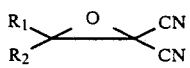

with an amine of the formula $R'NH_2$ in the presence of HX wherein
  $R_1$ is $pClC_6H_4$, $R_2$ is H, X is Br and R' is $CH_3CH_2$;
  $R_1$ is $pClC_6H_4$, $R_2$ is H, X is Br and R' is $CH_3$;
  $R_1$ is $C_6H_5$, $R_2$ is H, X is Cl and R' is $CH_3$;
  $R_1$ is $pClC_6H_4$, $R_2$ is H, X is Cl and R' is $C_6H_5$;
  $R_1$ is $pClC_6H_4$, $R_2$ is H, X is Cl and R' is $CH_3CH_2$;
  $R_1$ is $pMeC_6H_4$, $R_2$ is H, X is F and R' is H;
  $R_1$ is $pMeC_6H_4$, $R_2$ is H, X is Cl and R' is $CH_2CH_2OH$;
  $R_1$ is $pClC_6H_4$, $R_2$ is H, X is Cl and R' is $CH_2CH_2Cl$;
  $R_1$ is $pNO_2C_6H_4$, $R_2$ is H, X is Cl and R' is $CH_2CH_2Cl$;
  $R_1$ is $C_6H_5$, $R_2$ is H, X is Cl and R' is $CH_2CH_2Cl$; or
  $R_1$ is $pClC_6H_4$, $R_2$ is H, X is Cl and R' is $CH_2CH_2SCN$.

8. The process for forming an arylacetic acid ester of the formula

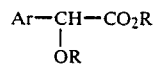

which comprises reacting a gem dicyanoepoxide of the formula

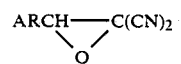

with an alcohol of the formula ROH in the presence of p-toluenesulfonic acid, wherein
  Ar is phenyl, R is $C_2H_5$;
  AR is phenyl, R is $(CH_3)_2CH$;
  Ar is $pNO_2C_6H_4$, R is $C_2H_5$ or
  Ar is $pClC_6H_4$, R is $C_2H_5$.

* * * * *